United States Patent [19]

Rose

[11] 3,979,459
[45] Sept. 7, 1976

[54] SUBSTITUTED 4-PHENYL BENZOPHENONES
[75] Inventor: John Brewster Rose, Letchworth, England
[73] Assignee: Imperial Chemical Industries Limited, London, England
[22] Filed: May 7, 1974
[21] Appl. No.: 467,797

[30] Foreign Application Priority Data
May 25, 1973 United Kingdom............... 25203/73
Mar. 14, 1974 United Kingdom............... 11442/74

[52] U.S. Cl. ................................................ 260/591
[51] Int. Cl.² ..................... C07C 49/80; C07C 49/82
[58] Field of Search ..................................... 260/591

[56] References Cited
UNITED STATES PATENTS
3,123,647  3/1964  Duennenberger et al. ......... 260/591
3,706,803  12/1972  Salle et al. ........................... 260/591

FOREIGN PATENTS OR APPLICATIONS
1,078,234  8/1967  United Kingdom
1,153,035  5/1969  United Kingdom OTHER PUBLICATIONS
Borsche et al, Chem. Abstracts 33, 1897[8] (1939).
Bachmann et al, J. Am. Chem. Soc. 57, 1095–1098 (1935).
Huntress et al, J. Am. Chem. Soc. 61, 526–527 (1939).

Primary Examiner—D. Horwitz
Attorney, Agent, or Firm—Cushman, Darby & Cushman

[57] ABSTRACT

Compounds of the formula

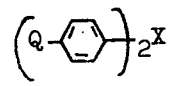

where X is

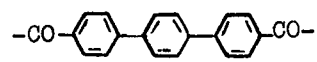

or a group having the formula

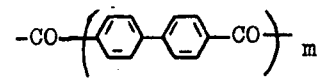

in which $m$ takes the value 1, 2 or 3 and where Q is fluorine, chloride, bromine or a hydroxyl group or alkali metal salt thereof. Compounds are also provided having the formula

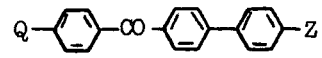

where Z is a hydrogen atom or a hydroxyl group (or alkali metal salt thereof) where Q is a hydroxyl group (or alkali metal salt thereof).

3 Claims, No Drawings

SUBSTITUTED 4-PHENYL BENZOPHENONES

This invention relates to aromatic ketones useful as starting materials for the production of aromatic polymers.

In British patent specifications Nos. 1,078,234 and 1,153,035 there are described processes in which aromatic polymers are prepared by nucleophilic polycondensation of bifunctional aromatic compounds with reactive bifunctional comonomers. In particular these specifications describe processes for preparing polyarylketones in which bis-(4-chlorophenyl) ketone could be used as starting material. British patent specification No. 1,078,234 also describes the preparation of polyaryl ketones in which the dipotassium salt of bis-(4-hydroxyphenyl) ketone is used as a starting material.

According to the present invention in one aspect there are provided, as valuable starting materials for preparing polyaryl ketones, compounds of the formulae

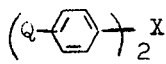

where X is

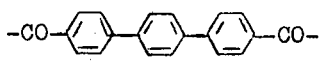

or a group having the formula

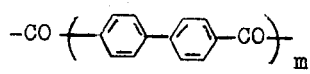

in which m takes the value 1, 2 or 3 and where Q is a fluorine, chlorine, bromine atom or a hydroxyl group or alkali metal salt thereof and may be the same or different.

The alkali metal may be any Group IA metal. If the alkali metal salt is used for polymerisation, the alkali metal is conveniently potassium or sodium, preferably potassium.

Displacement of alkali metal halide often occurs more readily if the potassium salt is used, but the weight (and usually the price) per mole of a potassium salt is higher than for the corresponding sodium salt. Some or all of the alkali metal cation in the reagent may be replaced by an organic onium cation having a positively charged heteroatom (for example a quaternary ammonium cation such as tetramethylammonium) stable under the conditions of the reaction, and the term "alkali metal salt" as used herein is deemed to refer also to salts containing such onium cations.

The compounds of the present invention where Q is fluorine, chlorine or bromine may be prepared by Friedel-Craft condensation of the appropriate 4-halobenzoyl halide onto the appropriate aromatic radical. For example 1. 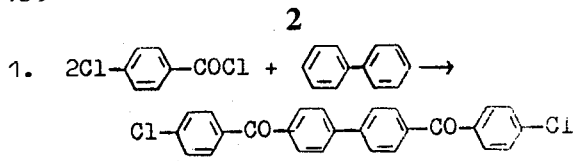

2. 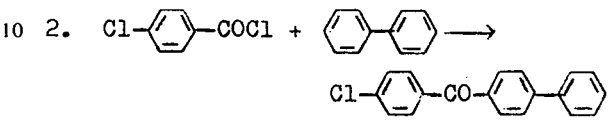

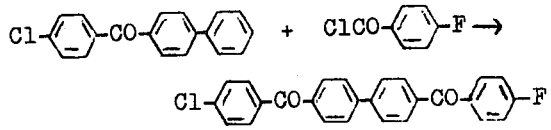

3. 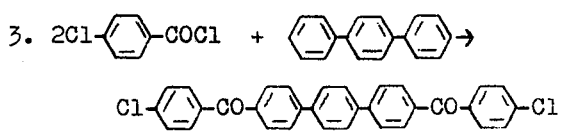

4. 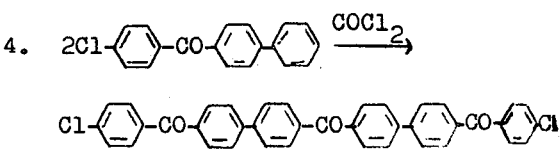

5. 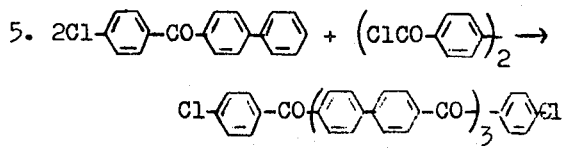

The compounds where Q is fluorine, chlorine and bromine can be hydrolysed to the corresponding bisphenols or their alkali metal salts. Where different halogen atoms are present in the molecule as in (2) above, they can be hydrolysed successively to give the corresponding halophenol or alkali metal salt thereof. The salt is capable of polymerisation as described in British patent specifications Nos. 1,153,035 and 1,177,183.

Alternatively the bisphenols may be prepared by Friedel-Craft condensation of a halocarboxy phenol protected by for example a carbonate or phosphorochloridate group with e.g. biphenyl, e.g. as in 6.

6. 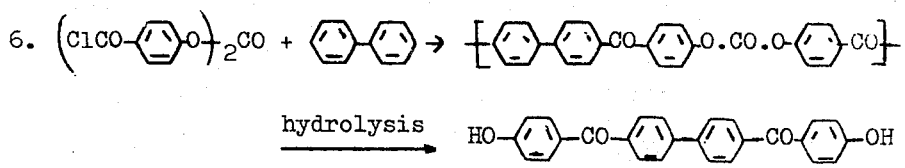

Accordingly as a further aspect of the present invention compounds having the formula are also provided

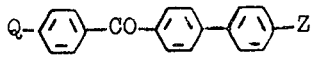

where Z is a hydrogen atom, or a hydroxyl group (or alkali metal salt thereof) when Q is a hydroxyl group (or alkali metal salt thereof). Such compounds where Z is a hydrogen atom may be prepared as described hereinbefore by Friedel-Craft condensation of 4-halobenzoyl chloride with equimolar amount of biphenyl in the presence of for example ferric chloride or preferably aluminum chloride as catalyst. Compounds where Z and Q are hydroxyl groups may be made by condensation under Friedel-Craft conditions of bis-(4-biphenyl) carbonate and bis-(4-halocarbonylphenyl) carbonate, followed by hydrolysis. The resulting bisphenol and its dialkali metal salt are useful in the production of polymers as described in Canadian patent specification No. 847,963 and British patent specification No. 1,078,234.

Hence in accordance with the present invention in one aspect, valuable monomers of the aforesaid formula

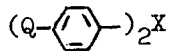

are provided for the preparation of homopolymeric and copolymeric polyaryl ketones using for example the routes described in the aforesaid specifications. The intermediates enable polymers to be produced which have a greater proportion of biphenylene and/or terphenylene units in the chain than has been possible according to the disclosures in the prior art above referred to, with the advantage that the polymers have among other valuable properties, higher Tg's. The Tg, the glass transition temperature (also commonly referred to as the second order transition temperature), is conveniently measured as the temperature at which there is an inflexion in the trace obtained in a differential scanning calorimeter when the polymer is heated at a predetermined rate, usually 16°C per minute. While an increase in biphenyl units is thought likely to give rise to polymers having desirably higher Tg's, the starting materials for polymerisation available hitherto for preparing polyaryl ketones have placed a limit on Tg's attainable.

The invention is illustrated by the following examples.

EXAMPLE 1

Biphenyl (77 g; 0.5 mole) and 4-chlorobenzoyl chloride (175 g; 1 mole) were dissolved in nitrobenzene (100 cm³) in a glass flask (capacity 500 cm³) fitted with nitrogen purge, condenser and stirrer and ferric chloride added (3 g; resublimed). The mixture was heated to 140°C and the reaction was followed by estimation of evolved hydrochloric acid (using titration against standardised sodium hydroxide solution). After about 85% completion of the reaction, the dark-violet reaction mass which contained some white crystals was poured into methanol (200 cm³) into which some acetyl acetone (2 g) had been dissolved. The product was filtered, washed with methanol and methyl ethyl ketone and finally recrystallised from dimethyl sulphoxide. The white crystals (38 g) had melting point 303°C to 304°C and infra-red and nuclear magnetic resonance spectra consistent with the formula

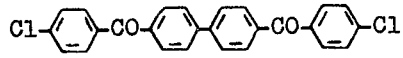

Polymer having reduced viscosity of 1.2 [as measured at 25°C in concentrated sulphuric acid (density 1.84) solution containing 1 g of polymer in 100 cm³ of solution] was prepared by heating anhydrous dipotassium salt of bis-(4-hydroxyphenyl) ketone (0.0746 moles) and the above dichloride (0.0300 moles) and bis-(4-chlorophenyl) ketone (0.0450 moles) for 17 hours. The absorbance of the sulphuric acid solution at 550 nm on a 10 mm cell was 1.49.

EXAMPLE 2

A sample of hydrated dipotassium salt of bis-(4-hydroxyphenyl) ketone equivalent to 0.06486 moles of pure bisphenate was charged together with recrystallised diphenyl sulphone (34 g) to a glass flask (capacity 250 cm³) fitted with stirrer, thermocouple probe, nitrogen purge and air condenser. The flask was flushed with nitrogen and heated on a solder bath at 230°C in order to dehydrate the dipotassium salt. After one minute, the pressure in the flask was reduced to 60 torr; after a further 15 minutes at 230°C, stirring was commenced and continued for a further 15 minutes. Water distilled from the resulting yellow slurry. The apparatus was filled with nitrogen and pressure therein increased to atmosheric. Bis-(4-chlorophenyl) ketone (13.0957 g, 0.05215 moles recrystallised), 4,4'-bis-(4-chlorobenzoyl) biphenyl (0.01304 mole, 5.6232 g, recrystallised) and diphenyl sulphone (5 g recrystallised) were charged to the flask, heated at 230°C for 16.75 hours with stirring under nitrogen and then polymerised at 330°C for 7 hours. After polymerisation bis-(4-chlorophenyl) sulphone (2 g) was added.

For isolation of the polymer the reaction mixture was cooled to room temperature, and then successively boiled twice with acetone, boiled with water containing 1% by volume glacial acetic acid, boiled with water, and boiled with methanol, each boiling lasted for 30 minutes. The polymer was then dried at 140°C for 3 hours at a pressure of 5 torr. The polymer had reduced viscosity of 1.45 and absorbance of 0.44. A sample of the polymer was compression-moulded at 420°C into film and cooled slowly. The resulting opaque film was tough and was creased repeatedly in all directions without cracking.

The polymer comprised 90% of units having the formula

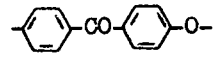

and 10% of units having the formula

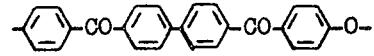

I claim:
1. A compound of the formula

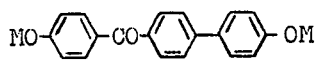

where M is hydrogen or alkali metal.

2. A compound of the formula

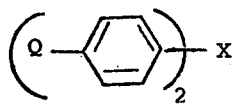

where X is a group having the formula

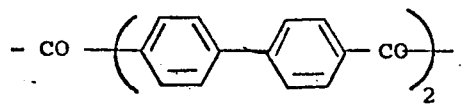

and Q is a fluorine, chlorine or bromine atom, a hydroxyl group or alkali metal salt thereof and may be the same or different.

3. A compound of the formula

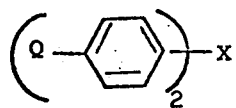

where X is a group having the formula

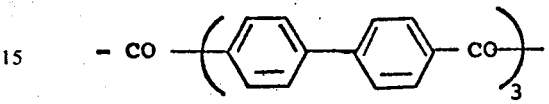

and Q is a fluorine, chlorine or bromine atom, a hydroxyl group or alkali metal salt thereof and may be the same or different.

* * * * *